United States Patent [19]

Huge

[11] 4,370,129

[45] Jan. 25, 1983

[54] TOOTH POSITIONER WITH HARDER AREAS

[75] Inventor: Gerald W. Huge, Racine, Wis.

[73] Assignee: Professional Positioners, Inc., Racine, Wis.

[21] Appl. No.: 275,002

[22] Filed: Jun. 18, 1981

[51] Int. Cl.³ .............................................. A61C 7/00
[52] U.S. Cl. ........................................................ 433/6
[58] Field of Search ............................................ 433/6

[56] References Cited

U.S. PATENT DOCUMENTS 3,211,143 10/1965 Grossberg ........................... 428/136
3,510,946 5/1970 Kesling .................................... 433/6

*Primary Examiner*—Robert Peshock

*Attorney, Agent, or Firm*—Wheeler, House, Fuller & Hohenfeldt

[57] ABSTRACT

Tooth positioner comprising several integral tooth engaging portions formed of materials having different hardness, the harder portions of which assist in anchoring the tooth positioner in its proper position in the patient's mouth.

Further, a method of making such tooth positioners by enclosing dental counterpart of the mold to form a first portion of the positioner, placing at least one other material into the mold in interfacing relation to the first portion to form a second portion of the tooth positioner, and curing the several materials into an integral body before extracting the positioner from the mold.

7 Claims, 8 Drawing Figures

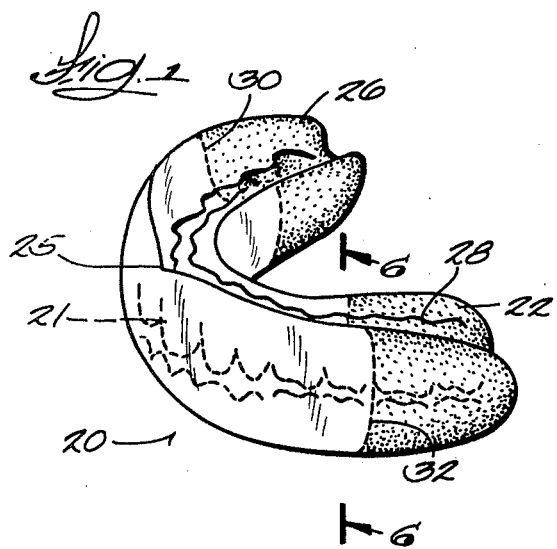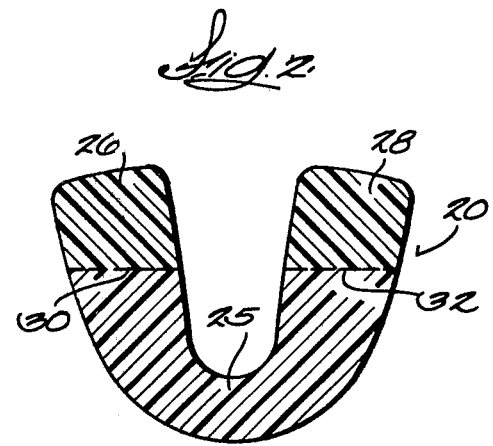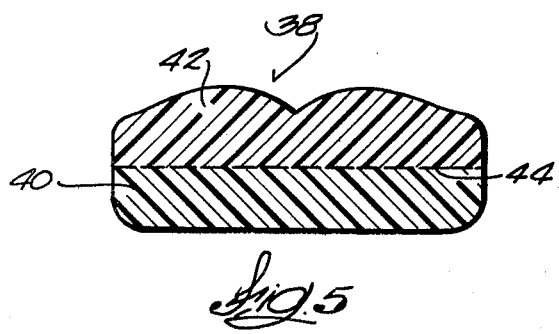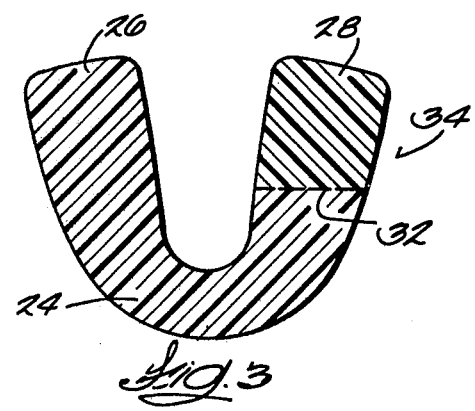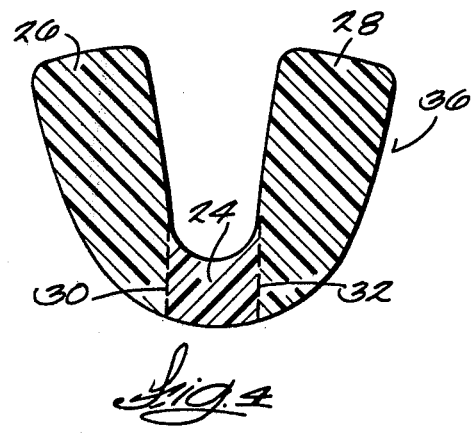

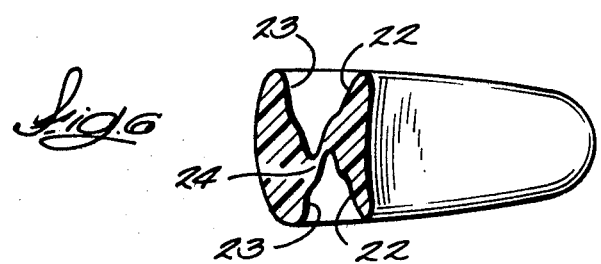
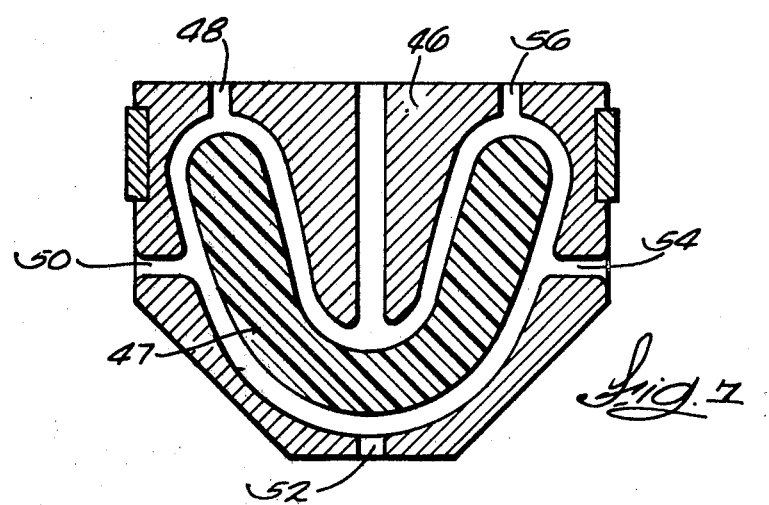
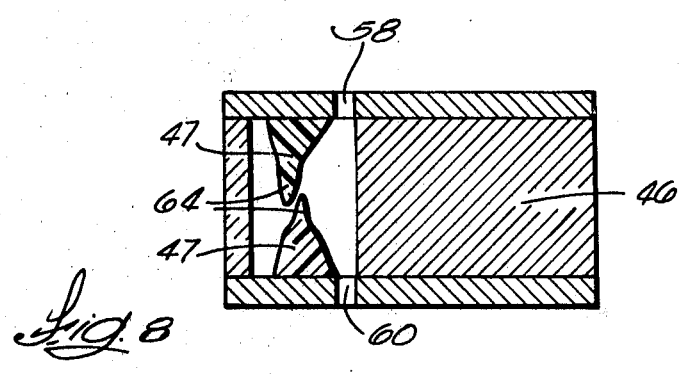

TOOTH POSITIONER WITH HARDER AREAS

TECHNICAL FIELD

The present invention is an improved appliance primarily for use in orthodontic procedures, known as a tooth positioner, and a method for manufacturing improved tooth positioners.

BACKGROUND ART

Tooth positioners are well known orthodontic appliances formed as an arch shaped body of resilient material fitting within a patient's mouth between the upper and lower arches. Tooth positioners have a generally concave surface for bearing on the buccal and labial surfaces of the teeth of at least one arch and a convex surface adjacent to the lingual surface of the patient's teeth. Tooth positioners for moving teeth into a more desired configuration are made by taking a cast of the upper and lower arches, moving teeth in the cast counterpart to more preferred positions, packing or pouring uncured material around the counterpart, curing this material to form a resilient arch shaped body, and trimming the outer surfaces of the body as necessary to make a finished appliance. Such tooth positioners are described, for example, in U.S. Pat. Nos. 2,467,432 and 2,531,222.

Such tooth positioners can be difficult to secure in the proper position in the patient's mouth, particularly when the tooth impressions in the positioner have been moved with respect to the existing positions of the patient's teeth. Deformation of such an appliance to fit it in the patient's mouth frequently creates stresses which tend to unseat or displace part of the tooth positioner from its proper position, thus limiting its therapeutic value. In prior art tooth positioners this seating problem has been addressed by providing protruding metal clips or hooks in the positioner to engage the patient's teeth. If properly anchored, such clips or hooks can assist in seating the positioner, but concentrate the force in very small areas. In some patients they may damage teeth or cause pain when the positioner is worn particularly if they terminate at or near the gum line. In another approach, taught in U.S. Pat. No. 4,055,895 (issued to Huge to Nov. 1, 1977), prestressed elastic bands are incorporated in the tooth positioner so that inward pressure, which can assist in seating the tooth positioner, is exerted on all the teeth of one or both arches. But in certain circumstances prestressed bands in the tooth positioner do not completely solve the seating problem.

Such tooth positioners also must have minimal bulk and weight, especially in the bite portions, to provide a correct and comfortable—or "anatomical"—fit. Yet, the positioners must be durable to resist bite-through and must have sufficient tensile strength and elasticity to move the patient's teeth to the desired positions. Previous positioners have not reached these goals, or have reached one at the expense of another.

Finally, tooth positioners have been made having two or more integrally formed portions of different hardness; one example of such a device is a tooth positioner made with relatively soft tooth engaging portions and a hard shell-like front to stiffen the appliance and to enable it to protect the patient's teeth while the device is worn. The harder part of the appliance does not engage the patient's teeth to assist in anchoring it in place.

SUMMARY OF THE INVENTION

The present invention is an improved tooth positioner comprising first and second integrally formed portions, one of which is harder than the other, engaging the patient's teeth. The harder and softer portions of the appliance can be variously arranged, so long as each portion engages at least one tooth in the patient's mouth. The harder portions can, for example, comprise a reduced bite portion or flange portion of the positioner to allow construction of an anatomical positioner which still resists bite-through and has adequate tensile strength. The harder portions can also anchor the positioner in place by engaging certain of the patient's teeth. The harder portion is that part of the tooth-engaging sockets that engage those teeth of the patient which are to serve as anchors and remain unmoved while the positions of other teeth are corrected primarily by engagement with the softer portions. Generally the molar teeth will be the anchors. The harder material should be Shore A Durometer 75 to 90, and the softer material 60 to 80 Shore, with a substantial difference between them. Wherever Shore hardness is referred to herein, Shore A hardness scale for elastomers is referred to.

My invention further includes the method of producing such articles by placing corrected tooth models in a container or flask, pouring one of the materials, allowing partial setting, pouring the other material, and curing to an integral resilient two-hardness body.

BRIEF DESCRIPTION OF DRAWINGS

FIG. 1 is a top perspective view of an improved tooth positioner.

FIG. 2 is a top plan view of the tooth positioner shown in FIG. 1.

FIG. 3 is a top plan view of an alternate tooth positioner.

FIG. 4 is a top plan view of another alternate tooth positioner.

FIG. 5 is a front elevation of still another alternate tooth positioner.

FIG. 6 is a cross section taken along line 6—6 in FIG. 1.

FIG. 7 is a cross section taken parallel to the occlusal plane of a molding flask and counterpart for making tooth positioners according to the present invention.

FIG. 8 is a cross section in the saggital plane of an alternate molding flask and counterpart.

DESCRIPTION OF PREFERRED EMBODIMENTS

Although the disclosure hereof is detailed and exact to enable those skilled in the art to practice the invention, the physical embodiments herein disclosed merely exemplify the invention which may be embodied in other specific structure. While the best known embodiment has been described, the details may be changed without departing from the invention, which is defined by the claims.

The tooth positioner 20 shown in FIGS. 1 and 2 is an arch shaped body of resilient material formed to fit within a patient's mouth between the upper and lower arches of teeth. Positioner 20 defines impressions such as 21 of the patient's teeth in their preferred positions in the patient's mouth. The lingual surfaces of the tooth impressions define convex flanges 23 adjacent the lingual surfaces of the teeth, while the buccal and labial surfaces of the tooth impressions define generally concave flanges 23 for bearing on the buccal and labial surfaces of the teeth of at least one arch. Referring briefly to FIG. 6, surfaces 22 and 23 are joined by a bite portion 24 which lies in the occlusal plane and receives the cutting surfaces of a patient's teeth when the positioner is worn. Portions of the bite portion and/or flanges can be formed of harder material having higher tensile strength and greater resistance to bite-through than the other parts of the positioner, as taught hereinafter, allowing their dimensions to be reduced. An anatomical positioner can thus be formed without compromising its strength or durability.

Returning to FIG. 1, one such structure having portions of differing hardness is shown. The tooth positioner has a proximal portion 25 which separates distal portions 26 and 28 made of different material than proximal portion 25, and the three portions of the tooth positioner are joined at interfaces 30 and 32 which lie in roughly vertical planes when the appliance is worn. Portions 25, 26, and 28 each are integral parts of the positioner, and each engages at least one tooth.

In one embodiment of the present invention the distal portions 26 and 28 of the positioner are formed from relatively harder resilient material to provide an anchor, while proximal portion 25 is formed of softer material. In an alternate embodiment of the invention the harder and softer materials may be exchanged. In either case the harder material can have a Shore A Durometer hardness of from about 75 to about 90, and the softer portion can have a Shore A Durometer hardness of from about 60 to about 80. In a preferred embodiment of the invention the harder portion is about 10 units harder than the softer portion of the Shore A Durometer scale. Materials harder or softer than those in the foregoing ranges can also be used. Also, appliances can have three or more portions having different hardnesses without departing from the scope of the present invention.

In tooth positioner 34 shown in FIG. 3 one distal end, 28, is joined to a second portion encompassing the proximal and distal portions 24 and 26 of the positioner, at interface 32. Again, either portion of positioner 34 can be harder than the other portion.

FIG. 4 shows another alternate embodiment 36 of the invention in which the interfaces 30 and 32 dividing the respective portions of the positioner 36 lie in generally vertical planes which are roughly perpendicular to the planes of the interfaces shown in FIGS. 2 and 3. FIG. 4 also illustrates that one or both distal portions of the appliance can vary in length.

FIG. 5 shows another alternate tooth positioner 38 having a lower portion 40 made of material having a different hardness than upper portion 42; the lower and upper portions are divided by interface 44 which in this embodiment is in the occlusal plane when the appliance is worn. Either portion may be harder than the other.

Although the tooth positioners of FIGS. 1 through 5 do not show any seating adaptations other than differential hardness, other seating devices, such as conventional clips or wires, integral or external resilient bands, rigid sockets, or the like may be included in the tooth positioner.

Each portion of the tooth positioner can be formed by pouring a liquid material into the mold flask 46 (FIGS. 7 and 8) containing a counterpart 47 when the mold is so oriented that the flat upper surface of the poured material is formed at the site of the intended interface with the next layer to be poured. Flask 46 is modified to the extent of making it fluid tight and providing sprues 48, 50, 52, 54, 56, 58, or 60, or any of them, to allow liquid materials to be poured or injected into the mold. Thus, if a tooth positioner as shown in FIGS. 1 and 2 is to be formed, the mold can be oriented so that the proximal teeth 64 of the counterpart are in the lowest part of the mold (as shown in FIG. 8). Next, the material to form the proximal portion 25 of the positioner is poured into the mold. Then the material to form the distal portions 26 and 28 is poured into the mold. After the respective portions of the positioner are poured, the positioner can be cured to a form retaining state. The mold and positioner are then separated to release the final tooth positioner. The positioner can be machined to provide outer surfaces having a pleasing and professional appearance.

To form the tooth positioners shown in FIGS. 4 and 5 from liquid raw materials the previously described procedure is used, but the mold is oriented differently while the respective materials are poured into it in order to provide interfaces in the finished product which have different orientations than those shown if FIGS. 1, 2, and 3. To form the structure shown in FIG. 4, the mold shown in FIG. 8 is rotated a quarter turn in the occlusal plane so that one distal end of the counterpart is above the other distal end and the arches are in a vertical plane. Access to the mold interior is provided by sprues at the upper distal end of the counterpart so that the first material can be poured into the counterpart. When the first material is poured into the mold, it flows into the lowermost distal end and forms a flat surface at the position of interface 32 as shown in FIG. 4. The material of the proximal portion of positioner is then poured into place. At least the just poured proximal portion of positioner is then cured sufficiently to retain its form, the mold is returned to the orientation shown in FIG. 8, and the other portion of the tooth positioner is cast.

The tooth positioner shown in FIG. 5 can be cast from liquid raw materials by orienting the assembled mold with its occlusal plane horizontal.

In an alternate method of forming the tooth positioners of the present invention, granular or bulk uncured solid materials (such as unvulcanized rubber) can be assembled in a mold flask in the desired positions and cured, fusing the several materials together to form an integral appliance. The compositions of the uncured compositions are varied so the same curing conditions yield regions of differing hardness. This method can be practiced using the well-known mold flasks for forming vulcanized tooth positioners.

The materials of the respective portions of the tooth positioner must be carefully selected to be compatible so that they will join to form an integral product, but one portion must not be allowed to diffuse so substantially into the next that the final appliance does not have separate portions of distinctly different hardness. If liquid raw materials are used, the necessary separation of materials can be accomplished by providing a second liquid material with a specific gravity no greater than that of the first liquid material, so gravity will not tend to mix the two liquid materials. Alternatively, the first liquid material poured into the mold can be partially or completely cured to harden it into a form retaining state before a subsequent material is poured into the mold. Thus, the material can be added as a liquid and readily conform itself to the mold surfaces, but it will act as a solid material when the next material is poured. Finally, if the materials have sufficiently high viscosities or are not liquids, they may not mix at a high enough rate to cause a problem.

One can also form a tooth positioner according to the present invention using incompatible adjacent materials if a thin adhesive layer which is compatible with both materials is inserted at the interface to bond the first and second incompatible materials together.

The materials used to form the tooth positioner are each formulated to cure to a specific hardness so that different portions of different hardness can be formed under the same molding conditions. Alternatively, a first portion can be placed in the mold and cured to provide a hard material, and subsequent material added to the mold can be cured under conditions which yield a softer cured mass, thus providing different hardnesses in the several portions of the tooth positioner.

The various tooth positioner configurations shown in the present disclosure are merely representative, as other configurations can be readily prepared by one skilled in the art of forming tooth positioners.

I claim:

1. In tooth positioner means comprising an arch-shaped body of resilient material having an integrally formed tooth engaging proximal region and first and second integrally formed tooth engaging distal regions, said tooth positioner means being formed to fit within a patient's mouth between the upper and lower arches, such means having a generally concave surface for bearing on the buccal and labial surfaces of the teeth of at least one arch and having a convex surface adjacent to the lingual surface of the teeth, the improvement wherein at least one of said proximal and distal regions of said arch-shaped body is an anchoring region composed of harder material than another of said proximal and distal regions.

2. The tooth positioner of claim 1, wherein at least one of said distal regions is composed of harder material than said proximal region.

3. The tooth positioner of claim 2, wherein each of said distal regions is composed of harder material than said proximal region.

4. The tooth positioner of claim 1, wherein said proximal region is composed of harder material than at least one of said distal regions.

5. The tooth positioner of claim 4, wherein said proximal region is composed of harder material than each of said distal regions.

6. The tooth positioner of claims 1, 2, 3, 4, or 5, wherein each harder region has a Shore Durometer hardness of from about 75 to about 90, and wherein at least one other region has a Shore Durometer hardness of from about 60 to about 80.

7. The tooth positioner of claim 6, wherein said harder region is about 10 Shore Durometer hardness units harder than at least one other of said distal and proximal regions.

* * * * *